United States Patent
Borodulin et al.

(12) United States Patent (10) Patent No.: US 6,544,240 B1
Borodulin et al. (45) Date of Patent: Apr. 8, 2003

(54) CATHETER FOR SELF-CATHETERIZATION WITH GUIDING MIRROR

(76) Inventors: German Borodulin, 583 -46$^{th}$ Ave., San Francisco, CA (US) 94121; Alexander Shkolnik, 485 Dartmouth Ave., San Carlos, CA (US) 94070; Ananias Diokno, 480 Hillspur Rd., Ann Arbor, MI (US) 48105

( * ) Notice: Subject to any disclaimer, the term of this patent is extended or adjusted under 35 U.S.C. 154(b) by 0 days.

(21) Appl. No.: 09/438,273

(22) Filed: Nov. 12, 1999

(51) Int. Cl.$^7$ .................................................. A61F 5/44
(52) U.S. Cl. ...................................... 604/329; 604/544
(58) Field of Search .............................. 604/517, 322, 604/326–331, 540, 544, 264

(56) References Cited

U.S. PATENT DOCUMENTS 5,653,700 A * 8/1997 Byrne et al. ................. 604/329

* cited by examiner

Primary Examiner—Anhtuan T. Nguyen
Assistant Examiner—Michael M Thompson

(57) ABSTRACT

A female urethral catheter for self-catheterization with catheter guiding means comprising: a tubular catheter body having a distal end for insertion into the patient's urinary bladder through the urethra, said distal end having a urine inlet opening; an opened proximal end not insertable into the urethra and used for discharging the urine taken from the urinary bladder; a sterile infection protective cap slidingly fit onto said distal end of said catheter, said cap having a slit on its distal end for possibility of pushing said catheter through said sterile tip into the bladder without physical contact of the catheter with the infectious front part of the urethra; and a combined mirror and catheter attachment means on the distal end of said cap to facilitate the patient in finding the position of the urethra meatus and for attachment of the catheter to the patient's after insertion of the cap into the urethra.

8 Claims, 4 Drawing Sheets

CATHETER FOR SELF-CATHETERIZATION WITH GUIDING MIRROR

FIELD OF THE INVENTION

The present invention relates to the field of urology, in particular to a catheter for self-catheterization.

BACKGROUND OF THE INVENTION

Patients who require intermittent self-catheterization may have low-motor and/or sensory type neurogenic bladders, detrusor-sphincter dyssynergia or underactive bladder from non-neurogenic causes such as obstruction or overdistention that result in the retention of urine. The urinary retention may be due to interference of nerve pathways in the brain or spinal column, or the peripheral nerves where nerve impulses control detrusor function and the process micturition. Neurologic bladder disease is frequently found in paraplegia, multiple sclerosis, cerebral vascular accidents, brain injuries, spinal cord lesions, trauma, infection or discogenic diseases affecting the sacral area of the spinal cord, extensive abdominal surgical operations and diabetes. non-neurogenic disturbances may be found in patients with infrequent voiding syndrome and post-operative or post-partum urinary retention.

It is customary for women with urinary retention to be prescribed intermittent catheterization by inserting a urethral catheter to void in the bathroom on a predetermined time schedule. Self-catheterization is normally performed every four to six hours because urine that remains in the bladder is prone to infection or stone formation.

However, some patients with multiple sclerosis often have fine-motor neuron dysfunction accompanied by visual impairment. Some patients are overweight and have a big belly which makes it difficult to see the urethral opening for insertion of the catheter into the urethra. This makes intermittent self-catheterization difficult if not impossible since the process generally requires the ability of the patient to have fine motor skills and good vision to locate the urethral meatus.

With presently available devices the patient accomplished self-catheterization with the aid of a separate mirror held at an appropriate angle, inserting the catheter along the urethra (about 3–4 cm) until its end reaches the bladder. The mirror must be held by the patient so that the self-catheterization thus becoming a two-handed operation, or the mirror must be supported in front of the patient in some way in a position whereby the patient has the required view. Additionally the catheter can be difficult to grip and manipulate, being only a thin, flexible plastic tube with a special slippery surface to aid insertion.

Attempts have been made to solve this problem by providing a catheter with a handle arrange essentially perpendicular to the catheter for manipulation of the catheter during insertion of the catheter into the urethra (see U.S. Pat. No. 5,653,700 Issued Aug. 5, 1997 to P. Byrne et al.). The handle has on its front surface a mirror made in the form of a thin film. According to the authors of the above patent, this mirror may be used to facilitate finding the meatus of the urethra for insertion of the catheter.

However, the handle makes the catheter, which is substantially a unidimensional thin tube, a two-dimensional device which occupies a large space in storage and is inconvenient for a self-catheterization patient who has to carry the catheter with her all the time. Furthermore, the handle is relatively thin and therefore the mirror cannot be wide enough to be practical for finding the location of the urethral meatus. In order to increase the size of the mirror, it would be necessary either to make the handle wider or to provide the handle with a special mirror attachment device. The device of the aforementioned patent is complicated in construction and expensive to manufacture.

It is known that the first part of the urethra is a harbor for infection. Therefore, during catheterization the urethral flora is pushed into the bladder, and this can initiate a urinary infection. An attempt has been made to solve the above problem by providing a device for self-catheterization with infection prevention means. Such a device is described in U.S. Pat. No. 5,147,341 issued to R. Starke in Sep. 15, 1992. This patent discloses a self-catheterization device comprising a flexible bag made of a thin transparent film, a sterilized cap attached to the bag, and a sterilized catheter located inside the bag and insertable into the urethra through the sterilized cap. In use, the sterilized cap, which is normally coated with a protective cover, is first inserted into the infectious part of the urethra and then the catheter is inserted into the bladder through the opening of the cap.

However, the device of U.S. Pat. 5,147,341 does not have means for finding the location of the urethral opening and therefore requires the use of a separate mirror. Furthermore, self-catheterization with this device is a two-handed operation.

OBJECTS OF THE INVENTION

It is an object of the present invention to provide a device for self-catheterization which combines means for finding the position of the urethral meatus with means for protection against infection and for making self-catheterization a single-handed operation. Another object is to provide a self-catheterization device of the aforementioned type which is simple in construction, reliable and practical in operation, and which releases the second hand for use in pushing the catheter into the urethra, if necessary.

SUMMARY OF THE INVENTION

A female urethral catheter for self-catheterization which is provided with a suction cup having a mirror inner surface and a sterile projecting central portion which functions as an infection-protective cap. A conventional urethral catheter is inserted into the hub portion of the cup and can be pushed through a slit formed at the proximal end of the infection-protective cap. In use for self-catheterization, a patient grips the cup with one hand by its hub portion, approaches it to the area of the urethra, and manipulates the cup so as find the image of the urethral opening. At the same time, the patient sees the tip of the cap. After locating the meatus of the urethra and while seeing the tip of the cap, the patient inserts the prelubricated sterile cap into the urethra. At the moment when the cap is inserted to its full depth, the suction cup comes into contact with the mucose surface around the urethra so that further pressure applied to the cup from the patient's hand displaces air from the space between the inner surface of the cup and the surface of the patient's body, whereby after being released the cup remains attached to the patient's body by suction. Now both hands of the patient are free so that the patient holds the catheter at its proximal end and pushed it into the urethra and further to the bladder via the slit of the cap by using both hands.

DETAILED DESCRIPTION OF THE INVENTION

Figure 1:
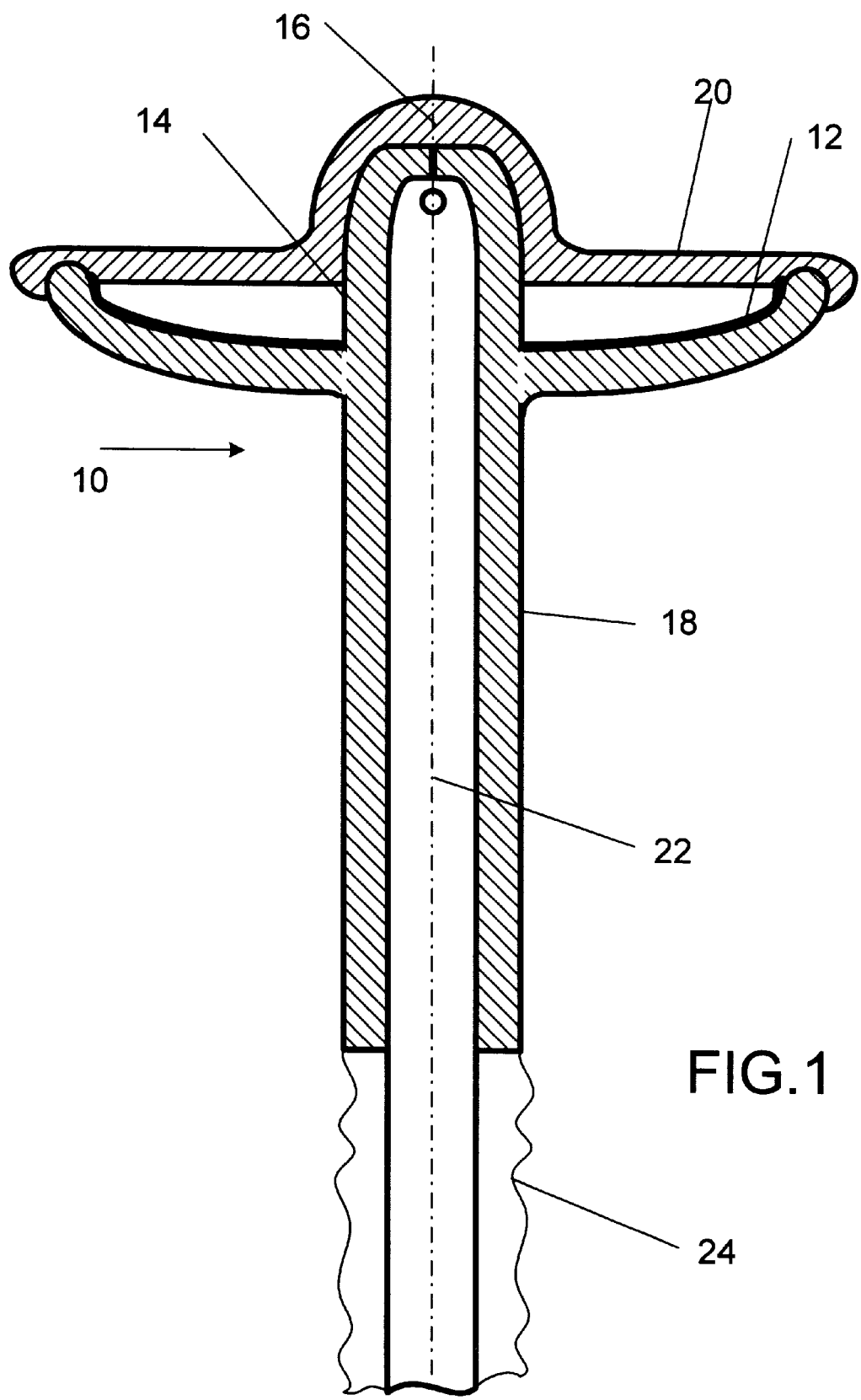
FIG. 1 is a longitudinal sectional view of a device for self-catheterization made in accordance with one embodiment of the invention.

FIG. 1 is a longitudinal sectional view which illustrates a device made in accordance with one embodiment of the invention. The device consists of a suction cup 10 having the inner surface coated with a mirror-like film 12 attached by means of an adhesive or applied by vacuum deposition or other methods known in the art. This suction cup can be temporary attached to a smooth surface, such as mucosa, e.g., the surface around the woman's urethra, by pressing it against this surface. This is the same principle as used for attaching a soap holder with suction cups to the surface of a glossy tile. On its front end the suction cup 10 has a hollow infection-protective cap 14 with a slit 16 on the distal end of the cap. On the rear side, the cup 10 has a hub portion 18. The cap 14 is sterile and can be protected by a removable thin-film cover 20 fitted onto the front end of the suction cup.

Inserted into the cap 14 through the hub 18 is a conventional tubular catheter 22. The body of the sterile catheter 22 can be protected from contact with non-sterile objects by a thin-film sheath 24 or thin-film urine-collecting bag (not shown) attached to the rear end of the hub 18. Prior to use of the device, the catheter 22 can be preinserted into the cap 14 so that the distal end of the catheter is inside the cap but does not protrude through the slit 16. If necessary, the cup 10 and the catheter can be held separately.

Directly prior to use, the patient (not shown) removes the cover 20 from the cup 10, grips the cup 10 with one hand by its hub portion 18, approaches it to the area of the urethra, and manipulates the cap so as find the image of her urethra. At the same time, the patient sees the tip of the cap 14. After locating the meatus of the urethra and while seeing the tip of the cap 14, the patient inserts the prelubricated sterile cap into the urethra. Normally the tip has a length of about ⅓ of the length of the woman's urethra since the front end of the woman urethra is the most infectious portion of the urethra. At the moment when the cap is inserted to its full depth, the suction cup 10 comes into contact with the mucose surface around the urethra so that further pressure applied to the cup 10 from the patient's hand displaces air from the space between the inner surface of the cup and the surface of the patient's body, whereby after being released the cup remains attached to the patient's body by suction. Now both hands of the patient are free so that the patient holds the catheter at its proximal end and pushed it into the urethra and further to the bladder (not shown) via the slit 16 of the cap by using both hands.

Since the cap 14 is sterile from outside and inside, the catheter passes into the bladder without any contact with infectious surfaces.

Thus, the cup 10 combines the functions of assisting in finding the urethra, of self-supporting the device on the patient's body, and of protection against infections.

Figure 2:
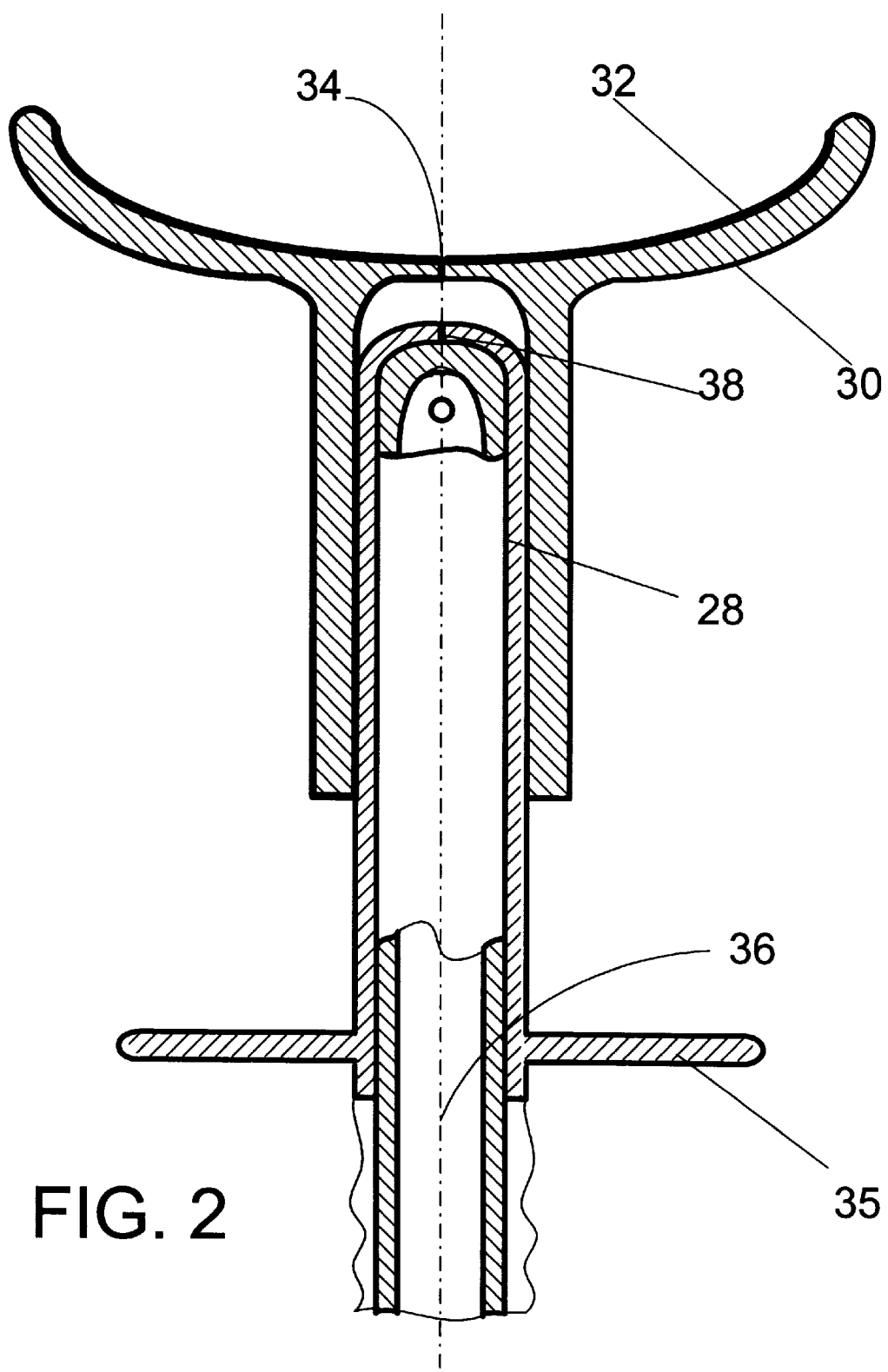
FIG. 2 is a longitudinal sectional view of a device for self-catheterization made in accordance with another embodiment of the invention.

FIG. 2 illustrates another embodiment of the invention, which differs from the embodiment of FIG. 1 in that the hub portion 26 is made longer and in that prior to use the entire cap 28 is located inside the hub 26. As a result, the entire inner surface of the suction cup 30, which is coated with a mirror film 32, can be used for finding the position of the urethral meatus. In other words, the mirror surface 32 is increased. The central portion of the suction cup 30 is covered with a portion of the aforementioned thin mirror film and has a slit 34. This slit presents no resistance to passing the catheter 36, whereas the slit 38 on the distal end of the cap 28 is more resistive to passing the catheter. The cap 28 has a flange 35 on its proximal end. As a result, when the catheter 36 is pushed forward, it shifts the cap forward and pushes it through the slit 34 so that the patient can see the tip of this cap simultaneously with the meatus of the urethra. The resistance of the slit 38 is sufficient to resist the force applied to the cap from the patient through the catheter for shifting the cap forward without passing the distal end of the catheter through the slit 34. The movement of the cap 28 is stopped when the flange 35 comes into contact with the rear end of the hub 26. The patient then pushes the cup forward for attaching it to her body in the same manner as described above. After the distal end of the cap is inserted into the urethra and the cup 30 is sucked to the patient's body in a manner described above, further application of the force to the catheter will overcome the resistance of the slit 38 so that the catheter will be guided into the urethra and into the bladder through the infection-protective cap 30. Since the cup 30 is attached to the patient body by suction after the cap 28 has been inserted into the urethra and since the catheter 36 has a tight sliding fit with the inner walls of the cap 30, the slit 34 will not violate sealing conditions within the suction cup.

If necessary, the hub portion 26 of the cup can be connected to a sterile urine-collecting bag 37.

Figure 3:
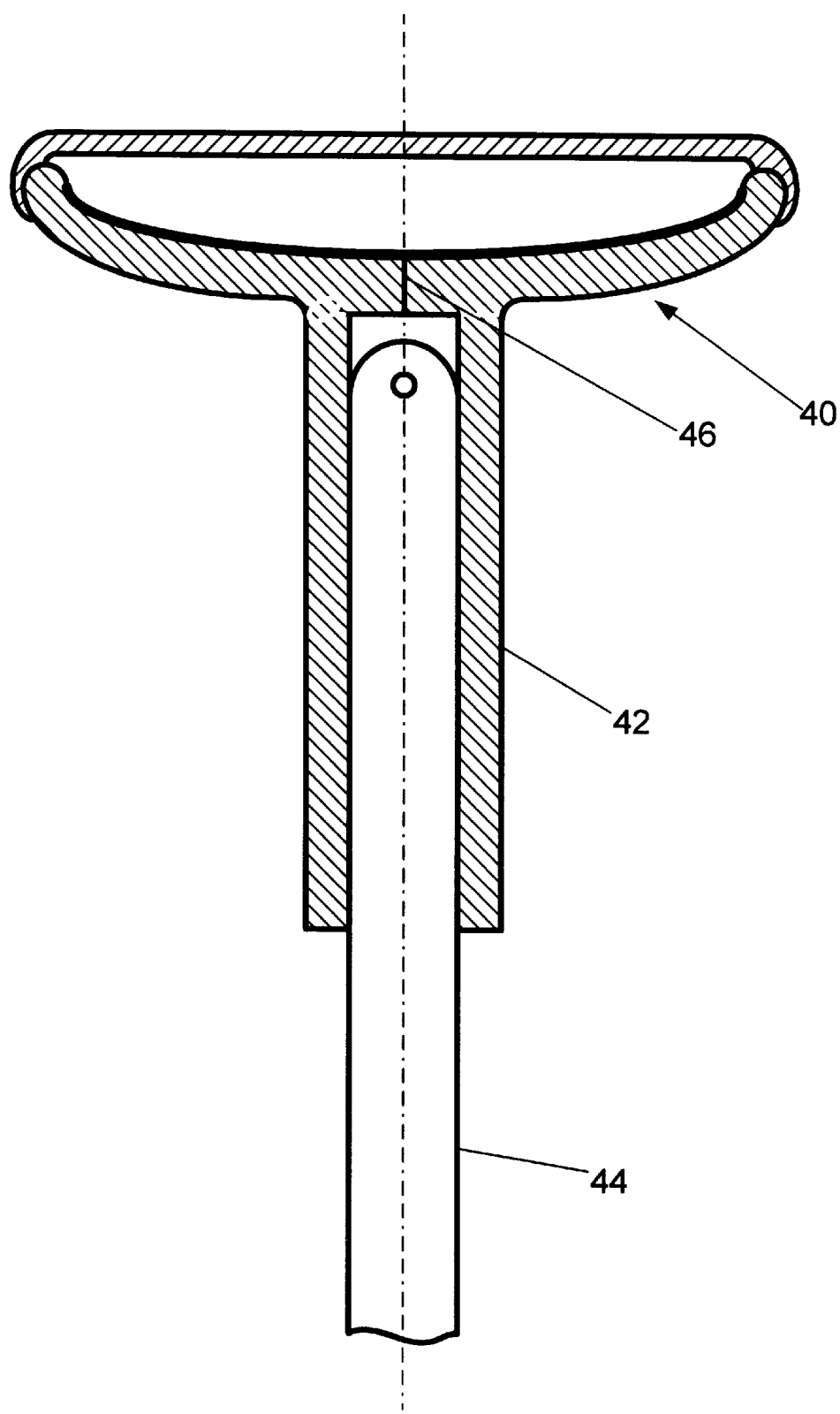
FIG. 3 is a longitudinal sectional view of a device for self-catheterization made in accordance with the third embodiment of the invention

FIG. 3 is a longitudinal sectional view of a catheter made in accordance with the third embodiment of the invention. According to this embodiment, the device may consist of a mirror-like suction cup 40 with the hub 42 and a catheter 44 inserted with a sliding fit into the hub 42, so that the cup 40 with the mirror inner surface can be used for finding the urethral meatus and for inserting the catheter directly into the urethra without the infection-protective cap. As in the previous embodiments, the mirror cup 40 has a slit 46 for passing the distal end of the urethral catheter into the urethra and bladder. Since the cup 40 is attached to the patient body by suction after the catheter 44 has been inserted into the urethra and since the catheter 44 has a tight sliding fit with the inner walls of the cup 40, the slit 46 will not violate sealing conditions within the suction cup. In this embodiment, the cup also fulfils two functions, i.e., locating the urethra and releasing both hands for manipulation with the catheter.

Figure 4:
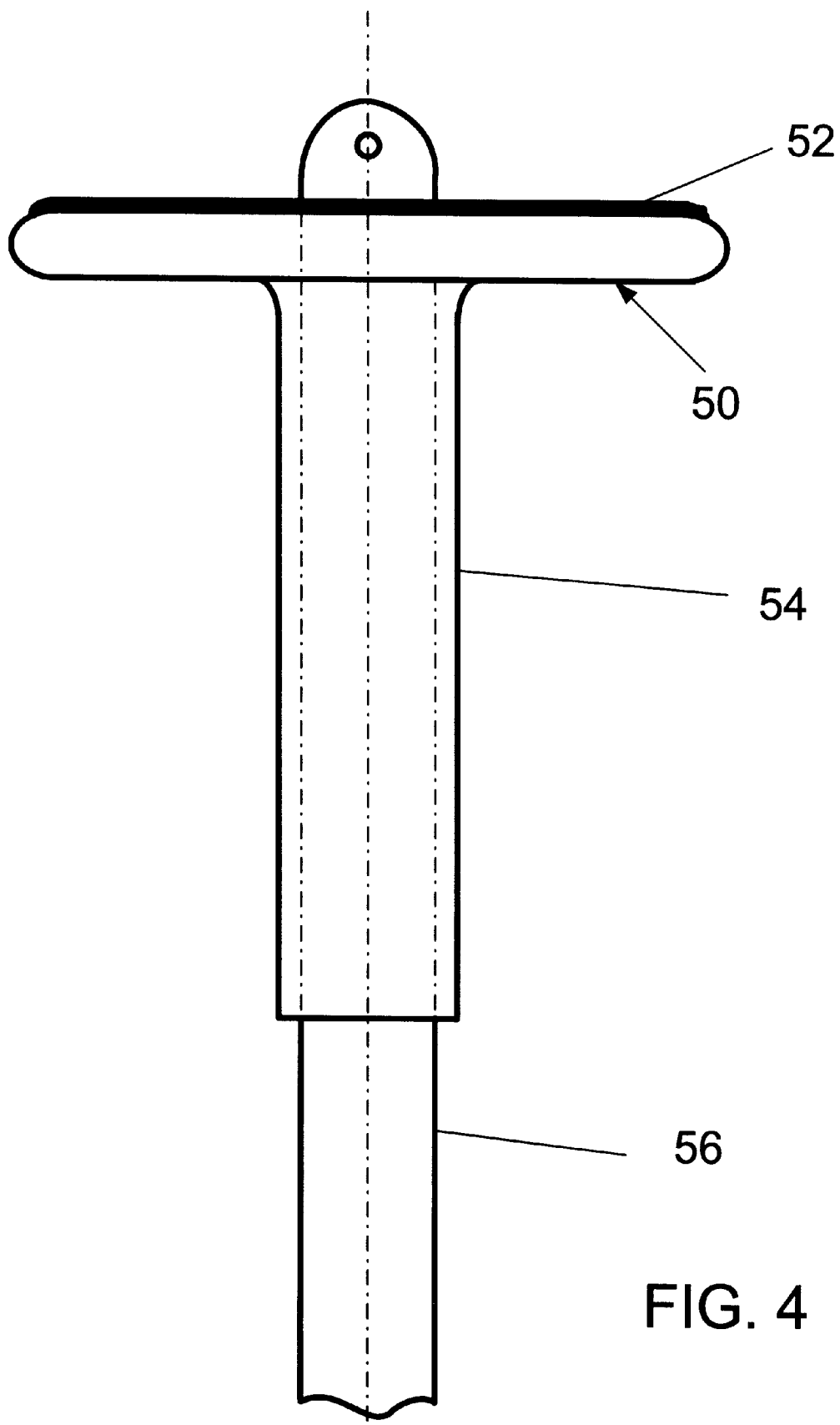
FIG. 4 is a longitudinal sectional view of a device for self-catheterization made in accordance with the fourth embodiment of the invention.

FIG. 4 shows a simplified version of the device of the invention. It consists of a simple flat mirror 50 having a front mirror surface 52. If necessary, mirror 50 may have a hub portion 54 with a central hole through the mirror 50. A urethral catheter 56 can be inserted through the hub portion 54 and through the mirror 50 into the urethra and urinary bladder by manipulating the mirror for finding the urethral meatus as has been described earlier.

Thus it has been shown that the invention provides a device for self-catheterization which combines means for finding the position of the urethral meatus with means for protection against infection and for making self-catheterization a single-handed operation. The device of the aforementioned type which is simple in construction, reliable and practical in operation, and releases the second hand for use in pushing the catheter into the urethra.

Although the invention was described with reference to specific embodiments illustrated in the accompanying drawings, it will be apparent that various modifications can be made without going beyond the spirit and scope of protection as defined in the appended claims. For example, the mirror portion may have a flat rectangular mirror. The probe means may be different from the urethral catheter. For example, it may be a straight female dilator, a vibratory bougie, etc. Different resistance to pushing the cap and the catheter can be provided due to different friction forces rather than due to different resistance in slits.

What is claimed is:

1. A female urethral catheter for self-catheterization comprising:

a tubular catheter body having a distal end for insetion into the patient's urinary bladder through the urethra, said distal end having a urine inlet opening and an opened proximal end not insertable into the urethra and used for discharging the urine taken from the urinary bladder; and a combined mirror and catheter attachment means on said dista end of said tubular catheter body to facilitate the patient in finding the position of the urethral meatus and for attachment of said female urethral catheter to the patient's body, said combined mirror and catheter attachment means having a front end and a rear end, wherein said combined mirror and catheter attachment means comprises a flexible suction cup on said front end with a slit for passing said tubular catheter body, and a hub portion on said rear end, said suction cup having a front end face and a mirror inner surface on said front end face.

2. The female urethral catheter of claim 1, wherein said mirror inner surface is formed by adhering a mirror film to said inner surface.

3. The female urethral catheter of claim 1, wherein said mirror inner surface is formed by vapor deposition.

4. The female urethral catheter of claim 1, further comprising a sterile infection-protective cap formed on said front end and insertable into the patient's urethra, said sterile infection-protective cap being slidingly fit onto said distal end of said tubular catheter body, said sterile infection-protective cap having a slit for possibility of pushing said tubular catheter body through said sterile infection-protective cap into the urinary bladder of said patient without physical contact of said tubular catheter body with the infectious front part of the urethra.

5. The female urethral catheter of claim 4, wherein said sterile infection-protective cap is made integrally with said flexible suction cup and extends forward in the distal direction from said flexible suction cup beyond the limits of said front end face of said flexible suction cup for insertion into the patient's urethra prior to contact between said flexible suction cup and the patient's body.

6. The female urethral catheter of claim 1, further comprising a sterile infection-protective cap insertable into the patient's urethra, said sterile infection-protective cap being slidingly fit into said hub portion, said flexible suction cup having a slit for pushing said infection-protective cap through said flexible suction cup.

7. The female urethral catheter of claim 6, wherein said slit of said flexible suction cup having resistance for pushing said sterile infection-protective cap with said tubular catheter body therethrough which is lower than resistance for pushing said tubular catheter body through said slit in said infection-protective cap, so that when said infection-protective cap is pushed forward through said slit of said flexible suction cup, said catheter remains inside said infection-protective cap.

8. The female urethral catheter of claim 6, wherein said cap has a flange on said rear end behind said hub for pushing said cap till contact with said hub in order to protrude said sterile infection-protective cap forward beyond the limits of said front end of said flexible suction cup.

* * * * *